(12) United States Patent
Federoff et al.

(10) Patent No.: US 11,728,042 B2
(45) Date of Patent: *Aug. 15, 2023

(54) DETECTING INFECTION USING SURROGATES

(71) Applicant: Georgetown University, Washington, DC (US)

(72) Inventors: Howard Federoff, Irvine, CA (US); Ophir Frieder, Chevy Chase, MD (US)

(73) Assignee: Georgetown University, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/406,598

(22) Filed: Aug. 19, 2021

(65) Prior Publication Data

US 2021/0383935 A1    Dec. 9, 2021

Related U.S. Application Data

(63) Continuation of application No. 16/996,303, filed on Aug. 18, 2020, now Pat. No. 11,232,869, which is a
(Continued)

(51) Int. Cl.
*G16H 50/80*    (2018.01)
*G16H 50/30*    (2018.01)
(Continued)

(52) U.S. Cl.
CPC .............. *G16H 50/80* (2018.01); *G10L 25/66* (2013.01); *G16H 40/67* (2018.01); *G16H 50/30* (2018.01)

(58) Field of Classification Search
CPC ........ G16H 50/80; G16H 40/67; G16H 50/30; G10L 25/66
See application file for complete search history.

(56) References Cited

U.S. PATENT DOCUMENTS 6,904,428 B2    6/2005  Frieder
8,321,372 B1 *  11/2012 Rakshit .................. G16H 50/30
                                                        706/62
(Continued)

FOREIGN PATENT DOCUMENTS

CN       111839462 A  * 10/2020  ............. A61B 5/743
DE    202018101544 U1 *  9/2018  ............. G16H 10/20
(Continued)

OTHER PUBLICATIONS

Hoilett, O.S., et al. (Jul. 2018). Kick LL: A Smartwatch for Monitoring Respiration and Heart Rate using Photoplethysmography. 2018 40th Annual International Conference of the IEEE Engineering in Medicine and Biology Society (EMBC). https://doi.org/10.1109/embc.2018.8513356. 11 pages.
(Continued)

*Primary Examiner* — Chico A Foxx
(74) *Attorney, Agent, or Firm* — Blank Rome LLP (57) ABSTRACT

A triage system that determines whether a user is likely to have contracted a disease based on sensor data received from a user device (e.g., a smartphone or activity tracker). Each symptom is identified by comparing sensor data to a predetermined baseline and comparing the difference to a predetermined symptom threshold. Because direct measurement of symptoms using the sensors available to the user may not be feasible or sufficiently accurate, the triage system also uses surrogates the identify certain symptoms. For example, a fever may be identified using heart data, a cough or shortness of breath may be identified by analyzing recorded sound, fatigue may be identified by analyzing the movement of the user device, and loss of smell or taste may be identified by recording sound and using speech detection algorithms to identify phrases in the recorded sound indicative of loss of smell or taste.

8 Claims, 3 Drawing Sheets

Related U.S. Application Data continuation of application No. 16/878,433, filed on May 19, 2020, now Pat. No. 10,902,955.

(60) Provisional application No. 63/019,025, filed on May 1, 2020.

(51) Int. Cl.
*G16H 40/67* (2018.01)
*G10L 25/66* (2013.01)

(56) References Cited

U.S. PATENT DOCUMENTS

| | | | |
|---|---|---|---|
| 9,945,672 | B2 | 4/2018 | Balasubramanian et al. |
| 10,049,183 | B2 | 8/2018 | Noh et al. |
| 10,198,779 | B2 * | 2/2019 | Pittman ............... G16H 50/80 |
| 10,275,526 | B2 | 4/2019 | Dodge et al. |
| 10,290,377 | B2 | 5/2019 | Bastide et al. |
| 10,362,769 | B1 | 7/2019 | Kartoun et al. |
| 10,937,296 | B1 | 3/2021 | Kukreja et al. |
| 11,056,242 | B1 | 7/2021 | Jain et al. |
| 11,087,886 | B1 | 8/2021 | Brown et al. |
| 2004/0236604 | A1 | 11/2004 | McNair |
| 2006/0019397 | A1 | 1/2006 | Soykan |
| 2008/0052318 | A1 | 2/2008 | Iliff |
| 2008/0064118 | A1 | 3/2008 | Porwancher |
| 2008/0126124 | A1 * | 5/2008 | Schechter ............. G16H 50/30 705/2 |
| 2008/0177571 | A1 | 7/2008 | Rooney et al. |
| 2009/0055217 | A1 | 2/2009 | Grichnik et al. |
| 2009/0222248 | A1 * | 9/2009 | Grichnik ............... G16H 50/20 703/11 |
| 2011/0066002 | A1 * | 3/2011 | Clawson ............... G16H 50/20 600/300 |
| 2013/0085079 | A1 | 4/2013 | Gill et al. |
| 2013/0166267 | A1 | 6/2013 | Kim et al. |
| 2013/0197090 | A1 | 8/2013 | Hewitt et al. |
| 2013/0204145 | A1 | 8/2013 | Shah |
| 2014/0196673 | A1 | 7/2014 | Menkes et al. |
| 2014/0259943 | A1 | 9/2014 | Nunn et al. |
| 2015/0100330 | A1 * | 4/2015 | Shpits ................... G16H 50/80 705/2 |
| 2015/0250396 | A1 | 9/2015 | Ahmed et al. |
| 2016/0091499 | A1 | 3/2016 | Sterling et al. |
| 2016/0132652 | A1 | 5/2016 | Chapman Bates et al. |
| 2016/0220165 | A1 | 8/2016 | Taherkhani et al. |
| 2016/0314185 | A1 | 10/2016 | Buchanan et al. |
| 2017/0039339 | A1 | 2/2017 | Bitran et al. |
| 2017/0061074 | A1 | 3/2017 | Singh et al. |
| 2017/0239459 | A1 | 8/2017 | Loudin et al. |
| 2017/0270262 | A1 | 9/2017 | Noh et al. |
| 2017/0316174 | A1 | 11/2017 | Wild |
| 2017/0325717 | A1 | 11/2017 | Dellimore et al. |
| 2017/0350702 | A1 | 12/2017 | Balasubramanian et al. |
| 2018/0144101 | A1 | 5/2018 | Bitran et al. |
| 2018/0303386 | A1 | 10/2018 | Hall et al. |
| 2019/0050510 | A1 | 2/2019 | Mewes et al. |
| 2019/0085394 | A1 | 3/2019 | Langston et al. |
| 2019/0148023 | A1 | 5/2019 | Sadilek et al. |
| 2019/0192086 | A1 | 6/2019 | Menon et al. |
| 2019/0209436 | A1 | 7/2019 | Ehrenpreis |
| 2019/0346459 | A1 | 11/2019 | Bowman et al. |
| 2019/0350852 | A1 | 11/2019 | Askari |
| 2020/0074313 | A1 | 3/2020 | Sharifi Sedeh et al. |
| 2020/0152330 | A1 | 5/2020 | Anushiravani et al. |
| 2020/0330045 | A1 | 10/2020 | Venkata Naga Sripada et al. |
| 2020/0411133 | A1 * | 12/2020 | Xu .......................... G16H 50/50 |
| 2021/0006933 | A1 | 1/2021 | Dean |
| 2021/0098128 | A1 * | 4/2021 | Neumann ............... G16H 50/30 |
| 2021/0121082 | A1 | 4/2021 | Wild |
| 2021/0327595 | A1 * | 10/2021 | Abdallah ............. A61B 5/02055 |
| 2022/0000375 | A1 * | 1/2022 | Meisal ..................... A61B 5/01 |
| 2022/0014592 | A1 * | 1/2022 | Kachare ................. H04L 67/12 |
| 2022/0037029 | A1 * | 2/2022 | Wu ........................ G16H 50/50 |
| 2022/0059242 | A1 * | 2/2022 | Schneider ............... H04W 4/38 |
| 2022/0122740 | A1 * | 4/2022 | Nematihosseinabadi .................... A61B 5/08 |

FOREIGN PATENT DOCUMENTS

| | | | | |
|---|---|---|---|---|
| GB | 2577725 | A * | 4/2020 | .......... A61B 5/0002 |
| KR | 102287364 | B1 * | 8/2021 | |
| WO | WO-2021163341 | A2 * | 8/2021 | |
| WO | WO-2021188043 | A1 * | 9/2021 | |
| WO | WO-2021217139 | A1 * | 10/2021 | |

OTHER PUBLICATIONS

Hu, Y., et al. (2020). Prevalence and severity of corona virus disease 2019 (COVID-19): A systematic review and meta-analysis. Journal of Clinical Virology, 127, 104371. https://doi.org/10.1016/jjcv.2020.104371. 8 pages.

Klopfenstein, T., et al. (2020). Features of anosmia in COVID-19 Médecine et Maladies Infectieuses. https://doi.org/10.1016/j.medmal.2020.04.006. 5 pages.

Karjalainen, J., et al. (1986) Fever and cardiac rhythm. JAMA Internal Medicine Jun. 1986;146(6):1169-71 https://www.ncbi.nlm.nih.gov/pubmed/2424378. 3 pages.

Li, K. et al. (2019) Spectral Analysis of Heart Rate Variability: Time Window Matters. Frontiers in Neurology, 10. https://doi.org/10.3389/fneur.2019.00545. 12 pages.

Porter, P., et al. (2019). A prospective multicentre study testing the diagnostic accuracy of an automated cough sound centred analytic system for the identification of common respiratory disorders in children. Respiratory Research, 20(1). https://doi.org/10.1186/s12931-019-1046-6. 10 pages.

Kobal, G., et al. (1996). "Sniffin' sticks": screening of olfactory performance. Rhinology. Dec. 1996;34(4):222-6. https://www.ncbi.nlm.nih.gov/pubmed/9050101. 14 pages.

Pascarella, G., et al. (2020). COVID-19 diagnosis and management: a comprehensive review. Journal of Internal Medicine. https://doi.org/10.1111/joim.13091. 15 pages.

\* cited by examiner

DETECTING INFECTION USING SURROGATES

CROSS-REFERENCE TO RELATED APPLICATIONS

This application is a continuation of U.S. patent application Ser. No. 16/996,303, filed Aug. 18, 2020, which is a continuation of U.S. patent application Ser. No. 16/878,433, filed May 19, 2020, now U.S. Pat. No. 10,902,955, which claims priority to U.S. Prov. Pat. Appl. No. 63/019,025, filed on May 1, 2020. The aforementioned patent applications are hereby incorporated by reference.

FEDERAL FUNDING

None

BACKGROUND

Viral pandemics (like the COVID-19 pandemic) require identification of infected individuals (testing) and identification of those who have had recent contact with infected individuals (contact tracing). However, the number of definitive virus tests and conventional testing sites are limited. Visiting medical caregivers or test center locations increases exposure to both caregivers and individuals being tested. Meanwhile, conventional contact tracing is a laboriously time-consuming process that requires a human to manually investigate the movements of each infected individual.

To address those concerns, definitive virus tests should be distributed to those at greatest risk, especially if the reservoir of infected individuals in the general population is unknown and determination of depth of reservoir is essential to safely manage population health. However, triaging potentially infected individuals is difficult for both health care practitioners and patients. Patients are often unsophisticated, untrained, and stressed. Patients at home do not have access to a medical practitioner and diagnostic equipment to make an informed determination of the likelihood that she or he has contracted the disease. The medical consensus regarding the symptoms that are associated with a novel disease can change over time.

Modern smartphones often include sensors that can be used to monitor the movements and environment of an individual. Wearable fitness tracking devices include even more sophisticated sensors that can be used to continually monitor the physiological parameters of users. Even when symptoms cannot be directly determined through sensor data, surrogates may be used to infer those symptoms. Meanwhile, software-based systems for triaging potential patients can be updated as new evidence emerges regarding the symptoms that are associated with a novel disease.

Finally, smartphones and wearable fitness tracking devices can be used to track the location of individuals and the other devices and individuals in those locations.

Accordingly, there is a need for a distributed system that detects the symptoms of a novel disease, using existing sensor technology and surrogates, and evaluates the likelihood that the user has contracted the novel disease. Ideally, the distributed system would provide a flexible platform such that software-based determinations can be revised as new medical evidence is revealed regarding the correlations between specific symptoms and the novel disease. Finally, the distributed system would ideally be capable of identifying and contacting those who have recently been in contact with individuals who are determined to have likely contracted the novel disease.

SUMMARY

In view of the aforementioned needs, a triage system is provided that determines whether a user is likely to have contracted a disease, based on sensor data received from a user device (e.g., a smartphone). The sensor data may be collected by an activity tracker in communication with the smartphone. The triage system identifies symptom(s) of the disease comparing sensor data to a predetermined baseline and comparing the difference between the sensor data and the predetermined baseline to predetermined symptom threshold(s).

As direct measurement of symptoms using the sensors available to the user may not be feasible or sufficiently accurate, the triage system also uses surrogates to identify certain symptoms. For example, the triage system may identify a fever based on heart rate or heart rate variability data. The triage system may identify a cough by recording sound and performing sound analysis of the recorded sound. The triage system may identify fatigue by analyzing the movement of the smartphone (or activity tracker). The triage system may identify shortness of breath (dyspnea) by analyzing respiratory rate data or pulse oxygenation data or recording sound and performing sound analysis of the recorded sound. The triage system may identify loss of smell or taste by recording sound and using speech detection algorithms to identify phrases in the recorded sound indicative of loss of smell or taste.

The triage system may also assist in contact tracing by recording the locations and networks joined by the user device. In response to a determination that the user is likely to have contracted the disease, the triage system may identify additional devices that were in close proximity with the user device (e.g., within a predetermined distance, within Bluetooth range, joined to the same local area network, etc.). The triage system may then be used to output information to those devices.

BRIEF DESCRIPTION OF THE DRAWINGS

Aspects of exemplary embodiments may be better understood with reference to the accompanying drawings. The components in the drawings are not necessarily to scale, emphasis instead being placed upon illustrating the principles of exemplary embodiments.

DETAILED DESCRIPTION

Reference to the drawings illustrating various views of exemplary embodiments of the present invention is now made. In the drawings and the description of the drawings herein, certain terminology is used for convenience only and is not to be taken as limiting the embodiments of the present invention. Furthermore, in the drawings and the description below, like numerals indicate like elements throughout.

System Architecture

Figure 1:
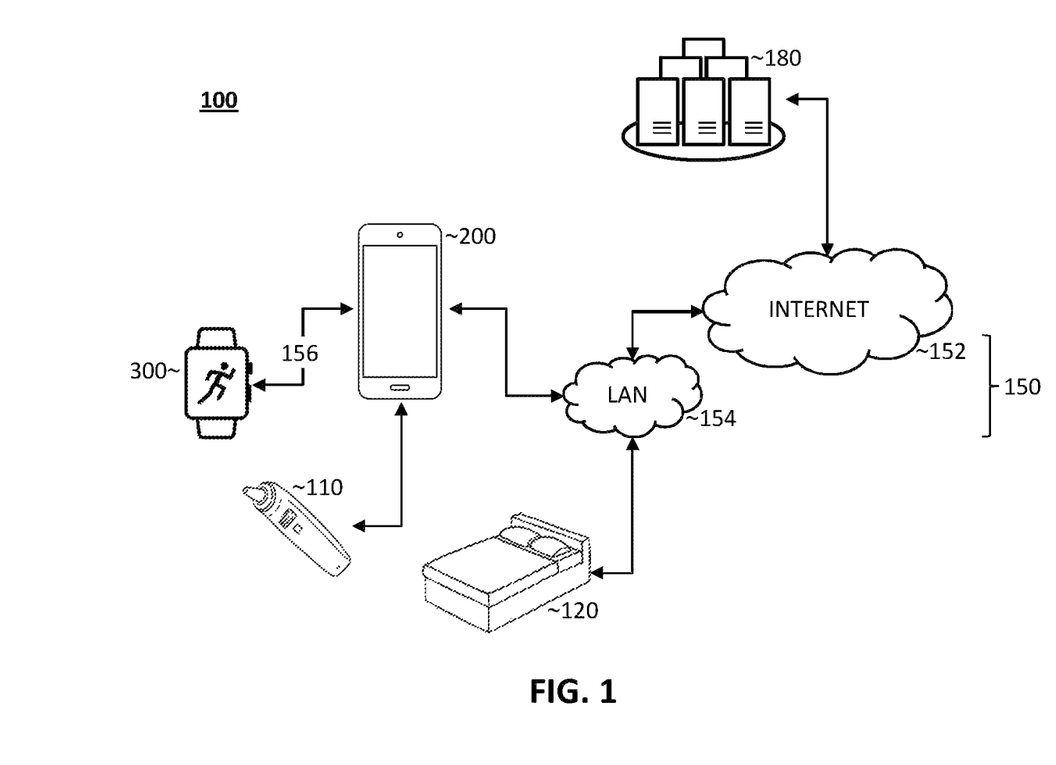
FIG. 1 is a diagram of an architecture of a COVID-19 triage system according to an exemplary embodiment of the present invention.

FIG. 1 is a diagram of an architecture 100 of a COVID-19 triage system according to an exemplary embodiment of the present invention.

As shown in FIG. 1, the architecture 100 includes a server 180 that communicates with a user device 200 (e.g., a smartphone) via one or more networks 150. Some users may also have access to a wearable electronic device 300 (for example, a fitness watch). The wearable electronic device 300 may communicate with the user device 200 via direct, short range, wireless communication signals 156 (e.g., Bluetooth). Additionally, some users may also have access to a body temperature thermometer 110 with functionality to wirelessly communicate with the user device 200 (e.g., via direct, short range, wireless communication signals 156 such as Bluetooth). Finally, some users may also have access to a sensor-enabled mattress or bed 120 with functionality to communicate with the user device 200 (e.g., via the local area network 152).

The server 180 may be any suitable computing device including, for example, an application server or a web server. The server 180 includes non-transitory computer-readable storage media, such as a hard disk or solid-state memory, and at least one hardware computer processor. In addition to internal memory, the server 180 may store data on external (non-transitory) storage media, which may be accessed via a wired connection, via a local area network, etc.

The networks 150 may include any combination of the Internet 152, cellular networks, wide area networks (WAN), local area networks (LAN) 154, etc. Communication via the networks 150 may be realized by wired and/or wireless connections.

The body temperature thermometer 110 may be any suitable device configured to sense the body temperature of the user and output information indicative of the user body temperature (as described, for example, in U.S. Pat. Pub. No. 2017/0061074 to Singh, et al.). The body temperature thermometer 110 may output information indicative of the user body temperature to the user device 200, for example, via direct, short range, wireless communication signals 156 (e.g., Bluetooth), via the local area network 152, etc.

The mattress or bed 120 may be any suitable device configured to determine the sleep state of a user lying on the mattress or bed 120 and output information indicative of the user sleep pattern (as described, for example, in U.S. Pat. Pub. No. 2014/0259434 to Nunn, et al.). The mattress or bed 120 may also detect the sleep posture of the user (e.g., prone, reclining at angle, etc.). The sleep posture of the user may be corelated with respiratory function.

Figure 2:
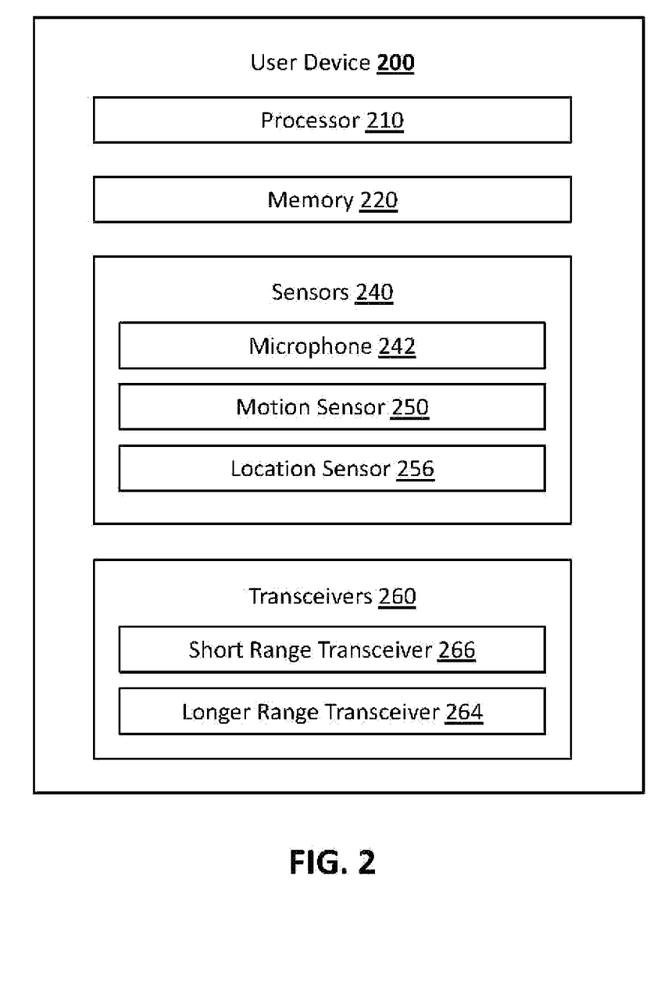
FIG. 2 is a block diagram of a user device according to an exemplary embodiment of the present invention.

FIG. 2 is a block diagram of the user device 200 according to an exemplary embodiment of the present invention. The user device 200 may be any suitable electronic device configured to send and/or receive data via the networks 150. The user device 200 may be, for example, a smartphone, a personal computer, a notebook computer, a personal digital assistant (PDA), a tablet, a network-connected vehicle, a wearable device, etc.

As shown in FIG. 2, the user device 200 includes at least one hardware processor 210 and memory 220. The user device 200 may also include one or more sensors 240 and one or more transceivers 260, which may be wireless transceivers. The sensor(s) 240 may include a microphone 242, one or more motion sensors 250 that detect motion by and/or orientation of the user device 200 (e.g., one or more multi-axes accelerometers and/or a gyroscope), a location sensor 256 (e.g., a global position system (GPS) chip), etc. The transceiver(s) 260 may include a short range, direct transceiver 266 (e.g., to communicate via Bluetooth) and/or a longer-range wireless transceiver 264 (e.g., to communicate via the local area network 154), etc.

Figure 3:
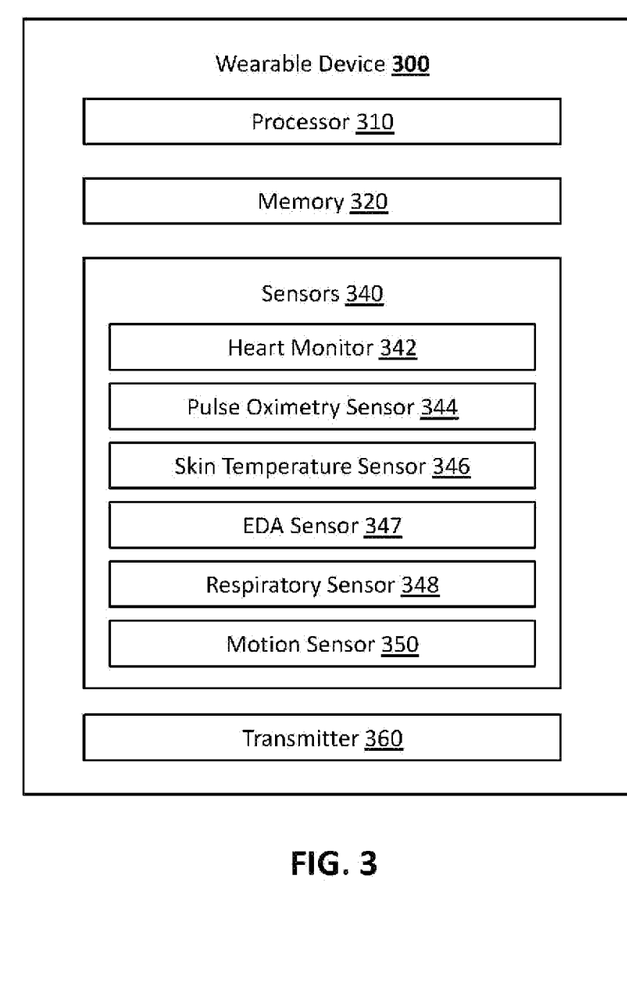
FIG. 3 is a block diagram of a wearable electronic device according to an exemplary embodiment of the present invention.

FIG. 3 is a block diagram of the wearable electronic device 300 according to an exemplary embodiment of the present invention.

As shown in FIG. 3, the wearable electronic device 300 includes at least one hardware processor 310 and memory 320. The wearable electronic device 300 may also include one or more sensors 340. The sensor(s) 340 may include a heart monitor 342 (e.g., a pulse sensor located proximate the radial artery as described in U.S. Pat. Pub. No. 2015/0250396 to Ahmed, et al.), a pulse oximetry sensor 344 (e.g., as described in U.S. Pat. Pub. No. 2015/0250396 to Ahmed, et al.), a skin temperature thermometer 346 (e.g., as described in U.S. Pat. Pub. No. 2015/0250396 to Ahmed, et al.), an electrodermal activity (EDA) sensor 347, sometimes referred to as a Galvanic Skin Response (GSR) sensor (e.g., as described in U.S. Pat. Pub. No. 2015/0250396 to Ahmed, et al.), a respiratory sensor 348 (e.g., as described in Hilett, O. S. et al.[1]), one or more motion sensors 350, such as one or more multi-axes accelerometers and/or a gyroscope (e.g., as described in U.S. Pat. Pub. No. 2015/0250396 to Ahmed, et al.), etc. The wearable electronic device 300 may also include a wireless transmitter 360 that outputs information from the one or more sensors 340 to user device 200, for example, via direct, short range, wireless communication signals 156 (e.g., Bluetooth), via the local area network 152, etc.

[1] Hoilett, O. S., et al. (2018, July). Kick LL: A Smartwatch for Monitoring Respiration and Heart Rate using Photoplethysmography. 2018 40th Annual International Conference of the IEEE Engineering in Medicine and Biology Society (EMBC). https://doi.org/10.1109/embc.2018.8513356

Briefly referring back to FIG. 1, the server 180 may provide a software program (e.g., a smartphone application) that is downloadable to the user device 200. The user device 200 and the server 180 may then cooperatively perform the software processing steps described below.

Health Monitoring

According to a systematic review and meta-analysis published on Apr. 14, 2020,[2] COVID-19 patients exhibit fever (86 percent of cases), cough (67 percent of cases), fatigue (42 percent of cases), and difficult or labored breathing, known as dyspnea (21 percent of cases). Additionally, it was found on Apr. 16, 2020,[3] that 47 percent of COVID-19 patients exhibit partial loss of sense of smell, known as hyposmia, or complete loss of smell, known as anosmia.

[2] Hu, Y., et al. (2020). Prevalence and severity of corona virus disease 2019 (COVID-19): A systematic review and meta-analysis. Journal of Clinical Virology, 127, 104371. https://doi.org/10.1016/j.jcv.2020.104371
[3] Klopfenstein, T., et al. (2020). Features of anosmia in COVID-19. Médecine et Maladies Infectieuses. https://doi.org/10.1016/j.medmal.2020.04.006

The COVID-19 triage system assesses the likelihood that the user has contracted COVID-19—and, by extension, the urgency with which the particular user should be tested directly—by detecting the aforementioned symptoms. In some instances, sensor data from the user device 200 (or wearable electronic device 300) may provide the COVID-19 triage system with direct evidence that the user is experiencing one of the symptoms. However, sensor data that provides direct evidence may not be available. Furthermore, even when direct sensor readings are available, that sensor data may not be sufficiently accurate for diagnostic purposes. Accordingly, the COVID-19 triage system also uses surrogates (i.e., indirect evidence that the user is experiencing one of the symptoms) to detect symptoms.

By relying on well established, medically documented, dominant symptoms (and discretizing measures that calibrate them), a machine learnable, interpretable assessment score can be computed. Using ethnic, racial, cultural, socio-economic factors and personal health comorbities, thresholds that indicate disease severity (e.g., uninfected, mild, moderate, and severe) can be established. As additional research regarding COVID-19 is published, the COVID-19 triage system provides a platform that can be updated so that the thresholds reflect the latest understanding of COVID-19 symptoms. In the event of a future epidemic or pandemic, the disclosed system provides a platform that can also be used to recognize the symptoms of a future virus, bacteria, parasite, engineered bioweapon, etc.

Like any evaluation system, the COVID-19 triage system recognizes deviations from established baselines. The COVID-19 triage system is initially configured with baseline metrics derived from the general population. For example, after the age of 10, the resting heart rate of an individual should range within 60 to 100 beats per minute with a regular rhythm; the normal body temperature should be approximately 37.0 degrees Celsius (98.6 degrees Fahrenheit). However, generalized norms may not be sufficient or fully accurate for diagnostic purposes. The normal body temperatures of individuals can range from 36.1 to 37.2 degrees Celsius. Similarly, blood pressure can vary from 90/60 mm Hg to 120/80 mm Hg. Therefore, when compared to generalized norms, an adult with a heart rate of 90 beats per minute, a body temperature of 37.2 degrees Celsius, or blood pressure of 119/79 mm Hg would be considered normal. However, those same symptoms would be considered alarming if the individual's personalized baseline were a heart rate of 60 beats per minute or a temperature of 36.1 degrees Celsius or a blood pressure of 91/61 mm Hg. Therefore, the COVID-19 triage system is preferably used to first obtain an individualized baseline for each user.

The COVID-19 triage system preferably establishes personalized baseline metrics for the user over a period of time while the user is known to be healthy. During this system training (onboarding) period, personalized baseline metrics for the user may be determined, including heart rate, blood pressure, pulse oxygen level, respiratory rhythm/rate, gait analysis (pace and frequency), sleep patterns, speech patterns, and/or other behavioral readings. The COVID-19 triage system may employ an active learning approach to continuously monitor the user over a period of time while the user is known to be healthy and make appropriate adjustments to the personalized baseline metrics for the user. If the COVID-19 triage system is not given the opportunity to perform system training while a specific user is known to be healthy (for example, if the specific user only starts using the COVID-19 triage system after the specific user suspects that she or he may be infected), the COVID-19 triage system may use default baseline metrics derived from the general population.

A method for detecting COVID-19 is described below using the five dominant symptoms identified by the two established, medically vetted articles described above; namely, fever, cough, fatigue, dyspnea, and anosmia. For each symptom, sensor-based measurements are taken (if available) and surrogates are used. As additional research regarding COVID-19 is published, the COVID-19 triage system provides a platform that may be used to identify additional symptoms (either through direct measurement or via surrogates). The COVID-19 triage system may also be updated so that the thresholds reflect the latest understanding of COVID-19 symptoms. In the event of a future epidemic or pandemic, the disclosed system can also be used to recognize the symptoms of a future virus or bacteria.

Fever detection. If available, a direct body temperature reading is collected and compared to the previously established baseline for the user. For example, body temperature readings from a body temperature thermometer 110 with wireless communication functionality may be transmitted to the user device 200 (e.g., via Bluetooth). Since a body temperature thermometer 110 with wireless communication functionality may not be available, the COVID-19 triage system may periodically prompt the user via the user device 200 graphical user interface to take his or her body temperature and manually input the body temperature reading via the user device 200 graphical user interface.

To continuously monitor the user without requiring the user to manually and periodically take her or his body temperature, a fever surrogate may be used. An increased heart rate is an indication of fever.[4] Therefore, the COVID-19 triage system may detect a fever by detecting the user's heart rate and comparing the detected heart rate to the baseline heart rate for the user. For example, data indicative of the heart activity of the user may be received, for example, from the heart monitor 342. The COVID-19 triage system may then determine the R-R interval of the user's heart activity, for example using a peak detection algorithm and/or a frequency analysis algorithm.

[4] Karjalainen, J., et al. (1986). Fever and cardiac rhythm. JAMA Internal Medicine 1986 June; 146(6):1169-71. https://www.ncbi.nlm.nih.gov/pubmed/2424378

Another sample fever surrogate is heart rate variability. Therefore, the COVID-19 triage system may detect a fever by performing a personalized heart rate variability analysis across periods when the user is active and periods when the user is inactive (at rest). Heart rate variability may be determined, for example, based on data received from the heart monitor 342. User activity may be determined, for example, based on data received from the motion sensors 250 of the user device 200 (or the motion sensors 350 of the wearable electronic device 300). For example, a spectral analysis via fast Fourier transforms may be used to determine if the heart rate of the user has increased.[5]

[5] Li, K. et al. (2019). Spectral Analysis of Heart Rate Variability: Time Window Matters. Frontiers in Neurology, 10. https://doi.org/10.3389/fneur.2019.00545

The difference between the user health metrics (body temperature, heart rate, or heart rate variability) and the (generalized or personalized) baseline is then converted into a single unitary metric indicative of the presence of (and, preferably, the probability or severity of) a fever. In some embodiments, the difference between the user health metric and the baseline may be compared to a threshold determined by the COVID-19 triage system to be indicative of the presence of a fever or multiple thresholds determined by the COVID-19 triage system to be indicative of the probability or severity of a fever. (In other embodiments, the differences between user health metrics and baselines may be clustered.) For example, the differences between the user health metric(s) and the baseline(s) may be compared to threshold(s) to determine one of the following unitary fever metrics:

TABLE 1

| Metric | Description |
| --- | --- |
| 1 | Health metrics inconsistent with fever |
| 2 | Heart rate variability impaired consistent with fever |
| 3 | Heart rate variability impaired with reported fever |

Cough detection. Coughs may be identifiable via acoustic engineering coupled with artificial intelligence. Using sound analysis, respiratory conditions are identifiable. For example, the detection of periodic paroxysmal (frequent and violent) coughing and irregular respirations is possible via the analysis of cough tonal quality.[6] Therefore, the COVID-19 triage system may record sound (via the microphone 242) and use artificial intelligence to detect coughing by the user.

[6] Porter, P., et al. (2019). A prospective multicentre study testing the diagnostic accuracy of an automated cough sound centred analytic system for the identification of common respiratory disorders in children. Respiratory Research, 20(1). https://doi.org/10.1186/s12931-019-1046-6

Again, the COVID-19 triage system identifies a single unitary metric indicative of the presence of (and, preferably, the probability or severity of) a cough. In this instance, determination is made by performing a sound analysis (e.g., using artificial intelligence). For example, the COVID-19 triage system may identify one of the following unitary cough metrics:

TABLE 2

| Metric | Description |
| --- | --- |
| 1 | Deviation from baseline not detected |
| 2 | Deviation from baseline indicates possible cough |

Fatigue detection. The COVID-19 triage system may detect fatigue by identifying deviations from the normal activity of the user. Additionally, the COVID-19 triage system may detect slowing or stopping along any daily movement, increasing the likelihood that the user is experiencing fatigue. Finally, the COVID-19 triage system may detect fatigue by comparing the amount of sleep the user is experiencing relative to the personalized baseline of the user (or determining if the user is sleeping for more than nine hours). User movement may be determined, for example, based on data received from the motion sensors 250 of the user device 200 (or the motion sensors 350 of the wearable electronic device 300). Whether the user is asleep may be determined based in drop skin temperature (for example, as measured by the skin temperature thermometer 346), galvanic skin response data (for example, as measured by the electrodermal activity (EDA) sensor 347), lack of activity (for example, according to data collected by the motion sensors 250) and/or reduced heart rate (for example, as measured by the heart monitor 342). Where available, whether the user is asleep may be determined based on data received from the sensor-enabled mattress or bed 120.

Again, the difference between the user health metrics and the (generalized or personalized) baselines are converted into a single unitary metric indicative of the presence of (and, preferably, the probability or severity of) fatigue. For example, the COVID-19 triage system may identify one of the following unitary fatigue metrics:

TABLE 3

| Metric | Description |
| --- | --- |
| 1 | Movement inconsistent with fatigue |
| 2 | Movement consistent with mild fatigue |
| 3 | Movement consistent with fatigue and excessive sleep |

Dyspnea detection. Difficulty or labored breathing (dyspnea) may be detected in multiple ways. If the relevant sensor data are available, the COVID-19 triage system may detect dyspnea by identifying an increased respiratory rate (for example, as measured by the respiratory sensor 348) and/or a change in blood oxygenation (for example, as measured by the pulse oximetry sensor 344). Additionally, as described above for detecting cough, acoustic engineering coupled with artificial intelligence may process breathing sounds to detect difficulty breathing. Also, the COVID-19 triage system may prompt the user (either audibly via the user device 200 speaker or visually via the user device 200 graphical user interface) to answer shortness of breath assessment questions (e.g., "How do you feel when walking to the bathroom?") and receive responses (either audibly via the user device 200 microphone or visually via the user device 200 graphical user interface). Again, the COVID-19 triage system may use the user health metrics or user responses to identify a single unitary metric indicative of the presence of (and, preferably, the probability or severity of) a dyspnea. For example, the COVID-19 triage system may identify one of the following unitary dyspnea metrics:

TABLE 4

| Metric | Description |
| --- | --- |
| 1 | Shortness of breath not detected |
| 2 | Breathing impaired, more with activity |

Anosmia, hyposmia, ageusia, and hypogeusia detection. The loss of the sense of smell (anosmia) and reduced ability to smell (hyposmia) have well established diagnostic tests, such as the University of Pennsylvania Smell Identification Test (UPSIT) and "Sniffin sticks", a test of nasal chemosensory performance based on pen-like odor-dispensing devices.[7] However, these tests are not likely to be readily available to the typical user. Therefore, the COVID-19 triage system employs a surrogate detection approach.

[7] Kobal, G., et al. (1996). "Sniffin' sticks":screening of olfactory performance. Rhinology. 1996 December; 34 (4):222-6. https://www.ncbi.nlm.nih-.gov/pubmed/9050101

The COVID-19 triage system may use passive vocal monitoring to determine if the user is making subjective complaints that are indicative of anosmia or hyposmia. For example, the COVID-19 triage system may record sound (captured by the microphone 242) and use speech detection algorithms to identify phrases like "I can't smell my coffee" or "I can't smell my breakfast", which are indicative of a loss of the sense of smell. Additionally or alternatively, the COVID-19 triage system may prompt the user (either audibly via the user device 200 speaker or visually the via the user device 200 graphical user interface) to answer questions about the user's capacity to smell. For example, the COVID-19 triage system may ask "Can you smell your toothpaste?" or "Can you smell your spice bottle of cinnamon?" or "Can you smell the cut onion?" and provide functionality for the user to subjectively answer questions that may be used to detect a loss of smell.

Similar to anosmia and hyposmia, the loss of sense of taste (ageusia) and reduced ability to taste sweet, sour, bitter, or salty substances (hypogeusia) can likewise be detected via surrogates. The COVID-19 triage system may use passive vocal monitoring to determine if the user is making subjective complaints that are indicative of ageusia or hypogeusia, such as "I can't taste my coffee" or "I can't taste my breakfast". Additionally or alternatively, the COVID-19 triage system may prompt the user (either audibly using the user device 200 speaker or visually the via the user device 200 graphical user interface) to answer questions about the user's capacity to smell, such as "Can you taste your toothpaste?" or "Can you taste salt or sugar?" or "Can you taste a cut onion?"

Again, the COVID-19 triage system may use the user phrases or user responses to identify a single composite metric indicative of the presence of the loss of taste or smell. For example, the COVID-19 triage system may identify one of the following unitary metrics:

TABLE 5

| Metric | Description |
| --- | --- |
| 1 | Smell (and/or taste) normal |
| 2 | Smell (and/or taste) impaired |

For each unitary symptom metric described above, a higher unitary symptom metric is indicative of a more severe (and/or higher likelihood that the user is experiencing) the respective individual COVID-19 symptom.

Detecting COVID-19

The COVID-19 triage system determines the likelihood that the user has contracted COVID-19 by weighing each of the unitary symptom metrics described above. The unitary metrics for each of the COVID-19 symptoms may be combined to form a composite metric indicating the likelihood that the user has contracted COVID-19. The unitary metric for each symptom may be weighted by the COVID-19 triage system based on the prevalence and correlation between each symptom and COVID-19, as identified in the latest medical documentation. For example, based on the two established, medically vetted articles described above, the weighting function employed by the COVID-19 triage system may be:

$$\text{Fever} * 0.86 + \text{Cough} * 0.67 + \text{Fatigue} * 0.42 + \text{Dyspnea} * 0.21 + \text{Anosmia} * 0.47 =$$

The composite metric for each user may be compared to one or more composite thresholds. The composite threshold(s) may be determined, based on the latest medical documentation, such that a composite metric below the lowest composite threshold is indicative of a low likelihood that the user has contracted COVID-19. Additional composite threshold(s) may be determined, again based on the latest medical documentation, indicative of higher likelihoods that the user has contracted COVID-19 (or indicative that the user is experiencing more severe symptoms of COVID-19).

The composite threshold(s) may be determined based on an analysis of the generalized population and/or, more preferably, individual characteristics of the user. The individual characteristics of the user may include age, gender, ethnic, racial, cultural, socio-economic status, personal comorbidities, etc. Geographically related indicators such as outbreak volume in a given location, e.g., New York City, might likewise be incorporated. Additionally, users may be asked to subjectively assess their level of interaction with other people, as the medical literature may indicate that more human interaction (for example, by users that work in a grocery store or nursing some) may put those users at higher risk. Given such considerations, the composite threshold(s) for each individual may altered. For example, given a patient with hypertension and diabetes, a "high severity" condition composite threshold might be set at a lower threshold value to account for the likely expected severity introduced by the comorbidities. Similarly, and possibly related, COVID-19 disproportionately affects the African-American community; thus, again, lower thresholds might be set to account for disease predominance should the user be African-American.

Because COVID-19 is novel, new studies are being published indicating new symptoms of the disease. As shown in a comprehensive review of COVID-19 diagnosis and management published on Apr. 29, 2020,[8] assessment for diagnostic care changes daily and the preponderance of symptoms varies across studies:

[8] Pascarella, G., et al. (2020). COVID-19 diagnosis and management: a comprehensive review. Journal of Internal Medicine. https://doi.org/10.1111/joim.13091

| | Guan et al. | Chen et al. | Shi et al. | Huang et al. | Yang et al. |
| --- | --- | --- | --- | --- | --- |
| Patients (n) | 1081 | 99 | 21 | 41 | 52 |
| Fever | 473 (44%) | 82 (83%) | 40 (98%) | 473 (44%) | 46 (89%) |
| Dyspnea | 205 (19%) | 31 (31%) | 9 (43%) | 22 (54%) | 33 (64%) |
| Cough | 745 (69%) | 81 (82%) | 15 (71%) | 31 (76%) | 40 (77%) |
| Sputum | 370 (34%) | — | 3 (14%) | 11 (27%) | — |
| Rhinorrhea | 53 (5%) | 4 (4%) | 5 (24%) | — | 3 (6%) |
| Sore Throat | 153 (14%) | 5 (5%) | — | — | — |
| Headache | 150 (14%) | 8 (8%) | 2 (10%) | 2 (5%) | 3 (6%) |
| Diarrhea | 42 (4%) | 2 (2%) | 1 (5%) | 1 (2%) | — |
| Nausea/vomiting | 55 (5%) | 1 (1%) | 2 (10%) | — | 2 (4%) |
| Myalgia | 164 (15%) | 11 (11%) | — | — | 6 (12%) |

[Table 1 of Pascarella, G., et al. (2020)]

To more accurately determine the likelihood that the user has contracted COVID-19, the process performed by the COVID-19 triage system may be updated to reflect the latest medical research. Therefore, the COVID-19 triage system provides a flexible platform that may be updated to identify additional symptoms that are found to be indicative of COVID-19. Those additional symptoms may be diagnosed by the COVID-19 triage system via direct sensor measurement, via surrogates, and/or through user responses to directed assessment questions (e.g., via the user device 200 graphical user interface). As additional studies are released, the COVID-19 triage system may also update the thresholds for the unitary metrics describing each of the symptoms above, the weights of each unitary metric, and/or the composite threshold(s).

The COVID-19 triage system may determine the likelihood that the user has contracted COVID-19 in response to a request by the user (e.g., via the user device 200 graphical user interface). The COVID-19 triage system may also be configured (with permission from the user) to periodically or continuously monitor the health metrics of the user and periodically determine (e.g., at least once per day) the likelihood that the user has contracted COVID-19.

The COVID-19 triage system may recommend that a user take certain actions based on the determined likelihood that the user has contracted COVID-19. For example, in response to a composite metric below a predetermined threshold, the COVID-19 triage system may output an indication that the user is unlikely to have contracted COVID-19 and may recommend that the user forgo further testing. However, in response to a composite metric greater than a predetermined threshold, the COVID-19 triage system may output an indication that the user is presumed to have contracted COVID-19 and recommend that the user obtain definitive virus testing and, later, serology testing for anti-Spike IgG.

To improve the COVID-19 triage system, users that are tested for COVID-19 may be encouraged to indicate the results of their test (e.g., via the user device 200 graphical user interface). Once a statistically significant sample of user health metrics and user test results have been received, the COVID-19 triage system may refine the unitary metric thresholds, the weights of each unitary metric, and/or the composite threshold(s) to better predict the likelihood that other users have contracted COVID-19. The COVID-19 triage system may use a (deep or shallow) machine learning process to adjust the unitary metric thresholds, the unitary metric weights, and/or the composite threshold(s).

Contact Tracing

The COVID-19 triage system may also be used to assist in a contact tracing process to identify persons who may have come into contact with users that have been infected with COVID-19. Accordingly, with permission of the user, the COVID-19 triage system may store records indicating the locations of the wearable electronic device 300 (if available) and/or the user device 200 (e.g., as determined by the location sensor 256). The COVID-19 triage system may also store records indicating the devices within range of short-range transceiver 266 of the user device 200 or the wireless transmitter(s) 360 of the wearable electronic device 300. The COVID-19 triage system may also store records indicating the local area networks 154 that the user device 200 (or the wearable electronic device 300) has joined.

In response to a determination by the COVID-19 triage system that the user is likely to have contracted COVID-19 (e.g., based on the symptoms described above), the COVID-19 triage system may determine the locations of the user during a time period when the user was likely to have been infectious (e.g., seven days prior to the determination that the user is likely to have contracted COVID-19). The COVID-19 triage system may also identify other devices in those locations during the time period when the user was likely to have been infectious. For example, the COVID-19 triage system may identify devices within a predetermined distance of the locations of the wearable electronic device 300 and/or the user device 200, devices within range of short-range transceiver 266 of the user device 200 or the wireless transmitter(s) 360 of the wearable electronic device 300, devices joined to the same local area networks 154 as the user device 200.

If the other devices in those locations are also employing the COVID-19 triage system, the COVID-19 triage system can contact those users (e.g., via the graphical user interface of their device, via email, etc.) to indicate that they may have been exposed to COVID-19 and make a recommendation to those users (e.g., that they should obtain definitive virus testing). Additionally, with permission from the user, the COVID-19 triage system may share device location information with organizations performing contact tracing. Therefore, the data collected by the COVID-19 triage system can contribute to a larger data set being used to trace contacts between infected individuals and others. For example, the COVID-19 triage system may indicate that a user (who is determined to have likely contracted COVID-19) was within range of another device. However, that device may not have the COVID-19 triage system installed and so the COVID-19 triage system may not be able to identify and contact the user of that device. However, the organizations performing contact tracing may be able to identify and contact the user of that device.

Users may also grant the COVID-19 triage system access to their calendar data and contact data (stored online or on the user device 200). The COVID-19 triage system may then be configured to contact individuals (e.g., using contact information stored on the user device 200 or accessible via the Internet) if calendar data indicates that he or she had an in-person meeting with a user that is presumed to have contracted COVID-19 during the time period when the user was likely to have been infectious. The COVID-19 triage system may also be configured to search the Internet or other data sources (e.g., employing a mediator-oriented search as described in U.S. Pat. No. 6,904,428 to Frieder, et al.) for individuals who may have had contact with the user during the time period when the user was likely to have been infectious.

The COVID-19 triage system may request permission from a user before contacting individuals who have been in contact with the user. Different message types may be sent to different individuals depending on the level of interaction, recency, length of contact, personal familiarity, etc.

Authority Data Transmission

Because global spread information is best derived from large scale data collection, the COVID-19 triage system may be configured to output information regarding user symptoms and/or behavioral patterns to a government or private health monitoring organization. Multiple electronic health record formats may be supported to provide flexibility of data transfer and subsequent analysis by the remote collecting party. The information transmitted (and the frequency of those transmissions) may be controlled by the user. Functionality may be provided for the user to terminate or change the information transmitted and/or the frequency of those transmissions at any time. Transmitted data may be anonymized. Data transmissions may be encrypted. The recipient of those data transmissions may be authenticated before the data are transmitted.

Privacy Protections

To preserve the user privacy, the COVID-19 triage system may require user registration and user permission before collecting sensor data and device location data. The COVID-19 triage system may also require user permission to access to user contacts and calendar data. The COVID-19 triage system may provide functionality for users to customize access rights (i.e., to individually grant or deny access to specific data types). User privacy may be further protected by encrypting all data collected, stored, and/or transmitted by the COVID-19 triage system. All data collected may be purged after a time period when that data no longer have diagnostic value. For example, if the COVID-19 triage system determines that the user is unlikely to have contracted COVID-19 as described above, the COVID-19 triage system may purge all previously-collected sensor data, determinations regarding the user's symptoms, and user location data.

Whenever possible, the sensor data described above may be collected and processed by the user device 200. However, certain processes described above (such as artificial intelligence or machine learning processes) may require the server 180 to receive sensor data indicative of user symptoms. In those instances, the sensor data transmitted by the user device 200 may be anonymized and/or encrypted.

Information and Incentives

The COVID-19 triage system is uniquely capable of providing valuable health-related information, which can be highly targeted based on the health status and location of the user. For example, the COVID-19 triage system may provide links to current literature and current status (e.g., locations and waiting times) of treatment centers, etc.

Potential users may also be incentivized to use the COVID-19 triage system. A heath care organization may offer free or reduced cost testing or medical treatment if an individual is diagnosed using the COVID-19 triage system. Monetary rewards may be provided to "friends and family." Commercial vendors (e.g., pharmaceutical companies) may be motivated to provide resources to users of the COVID-19 triage system to increase awareness of their products.

One barrier to widespread adoption of the COVID-19 triage system may be the availability of smart devices, such as smartphones and activity trackers. As these devices are now inexpensive, they may be provided (either free or subsidized as economically necessary) to incentive use of the COVID-19 triage system. Additionally or alternatively, the COVID-19 triage system may include web-based implementations that can be run on less expensive, Internet-connected devices (e.g., Chromebooks).

Language Support

English usage is common but not universal. Therefore, the COVID-19 triage system may support multiple language interactions, potentially via automated real-time translation based on deep learners as is known in the art. Support may also be provided for "minimal use" languages to support cultural differences.

Process

Figure 4:
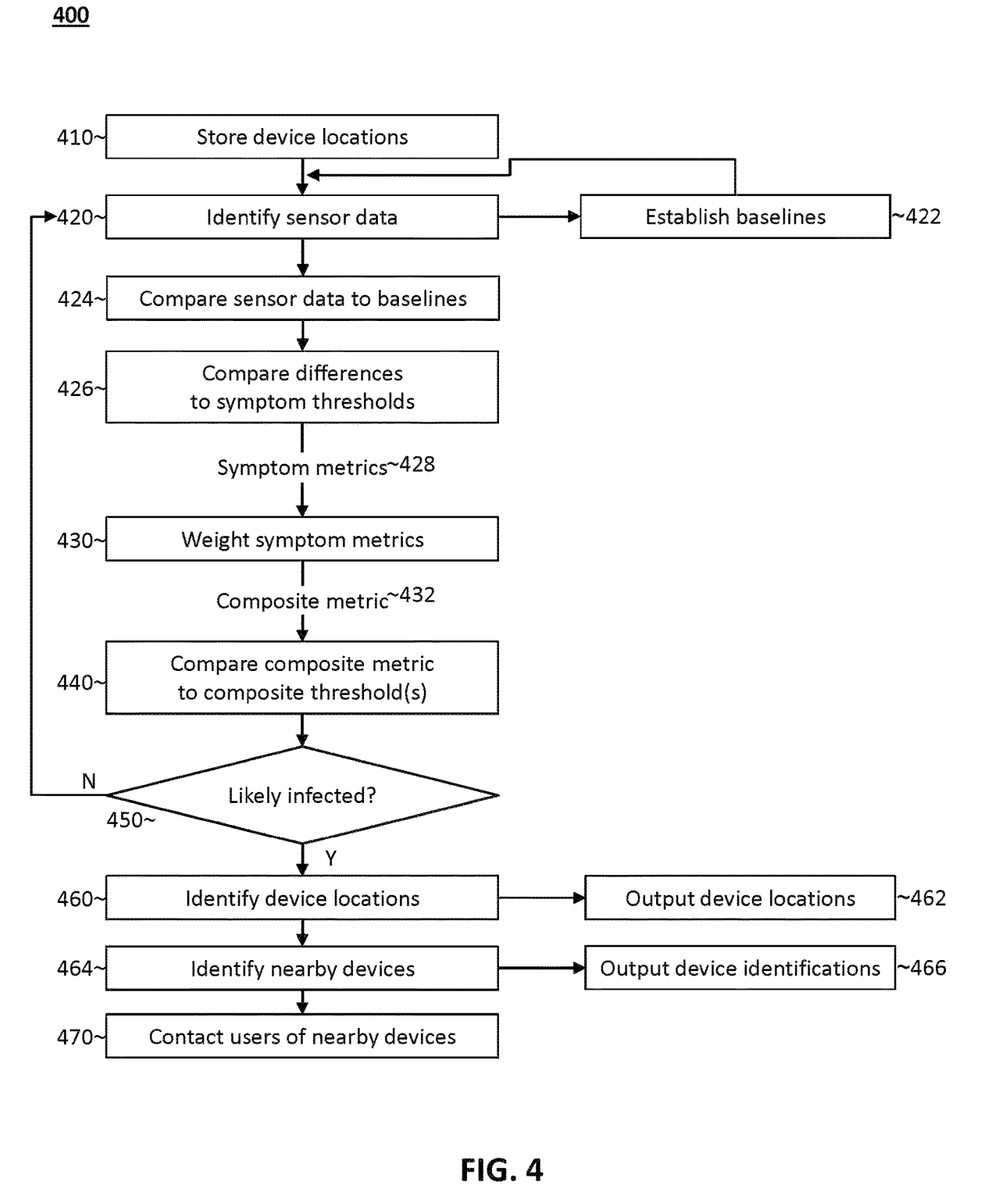
FIG. 4 is a flowchart of a disease detection and contact tracing process according to an exemplary embodiment of the present invention

FIG. 4 is a flowchart of a disease detection and contact tracing process 400 according to an exemplary embodiment of the present invention. As briefly mentioned above, the process 400 may be performed by the server 180 in conjunction with the user device 200 (e.g., running a software program provided by the server 180). As mentioned above, many of the steps of the process 400 require user authorization.

Locations of the user device 200 (and, if available, the wearable electronic device 300) are stored in step 410. The locations of the user device 200 may be determined by the location sensor 256. The locations of the user device 200 (or the wearable electronic device 300) may also include the local area networks 154 that the user device 200 (or the wearable electronic device 300) has joined and the identify of other devices within range of short-range transceiver 266 of the user device 200 or the wireless transmitter(s) 360 of the wearable electronic device 300.

Sensor data are identified in step 420. The sensor data may be collected by the sensors 240 of the user device, the sensors 340 of the wearable electronic device 300, the body temperature thermometer 110, the sensor-enabled mattress or bed 120, etc.

Baselines are established in step 422. By default, baselines derived from the general population may be used. More preferably, however, personalized baselines are established using sensor data collected from the user over a period of time while the user is known to be healthy. The process 400 then returns to step 420 and collects more sensor data.

The updated sensor data are compared to the baselines in step 424. The differences between the sensor data and the baselines are compared to symptom thresholds in step 426 to form symptom metrics 428. As described above, in some instances the sensor data may provide direct evidence that the user is experiencing one of the symptoms. However, other sensor data also provides surrogates (indirect evidence that the user is experiencing one of the symptoms) that can be used to form a symptom metric 428.

The symptom metrics 428 are weighted in step 430 to form a composite metric 432. The composite metric 432 is compared to composite threshold(s) in step 440 to determine the likelihood that the user has contracted the disease. If, based on the composite metric 432, the user is unlikely to have been infected (step 450: No), the process 400 returns to step 420 and updated sensor data are collected.

If, based on the composite metric 432, the user is likely to have been infected (step 450: Yes), the locations of the user device 200 (and wearable electronic device 300) during a time period when the user was likely to have been infectious are identified in step 460. As mentioned above, those locations may be geographic coordinates, local area networks 154 that the user device 200 (or the wearable electronic device 300) joined, and the identity of other devices within range of short-range transceiver 266. Those device locations may be output to an organization performing contact tracing in step 462.

Other devices in those locations during the time period when the user was likely to have been infectious are identified in step 464. Those other devices may have been devices within a predetermined distance of the locations of the wearable electronic device 300 and/or the user device 200, within range of short-range transceiver 266 of the user device 200 or the wireless transmitter(s) 360 of the wearable electronic device 300, or devices joined to the same local area networks 154 as the user device 200. Users of the other devices are contacted in step 470.

While a preferred embodiment has been set forth above, those skilled in the art who have reviewed the present disclosure will readily appreciate that other embodiments can be realized within the scope of the present invention. Disclosures of specific technologies are also illustrative rather than limiting. Therefore, the present invention should be construed as limited only by the claims.

What is claimed is:

1. A computer implemented method for determining whether a user is likely to have contracted a disease, the method comprising:
   receiving sensor data from a user device;
   receiving and storing locations of the user device;
   for each of a plurality of symptoms of the disease,
      calculating a symptom metric indicative of the likelihood that the user is experiencing the symptom by comparing the sensor data to a predetermined baseline and comparing a difference between the sensor data and the predetermined baseline to at least one predetermined symptom threshold;
weighing each of the symptom metrics to form a composite metric indicative of the likelihood that the user is likely to have contracted the disease; and
determining whether the user is likely to have contracted the disease by comparing the composite metrics to one or more predetermined composite thresholds, wherein:
the plurality of symptoms include anosmia or ageusia; and
the sensor data comprises sound, recorded by a microphone, that is analyzed using speech detection algorithms to identify phrases in the recorded sound indicative of anosmia or ageusia.

2. The method of claim 1, further comprising:
providing functionality, via a graphical user interface, to identify the plurality of symptoms of the disease, adjust one or more of the predetermined symptom thresholds, adjust the weights of one or more of the symptom metrics, and/or adjust the one or more predetermined composite thresholds for each symptom of the disease identified via the graphical user interface.

3. The method of claim 1, further comprising:
in response to a determination that the user is likely to have contracted the disease, identifying additional devices in the location of the user device and outputting information to the users of the additional devices.

4. The method of claim 3, wherein receiving the locations of the user device and identifying additional devices in the location of the user device comprises:
identifying the additional devices within range of the user device via direct, short range, wireless communication signals; or
identifying local area networks joined by the user device and the additional devices joined to the local area network.

5. A system for determining whether a user is likely to have contracted a disease, the system comprising:
a server in network communication with a user device;
a software application that is downloadable to and executable by the user device;
non-transitory computer readable storage media storing instructions that, when executed by the server and/or user device, cause the system to:
receive sensor data from the user device;
store locations of the user device;
for each of a plurality of symptoms of the disease, calculating a symptom metric indicative of the likelihood that the user is experiencing the symptom by comparing the sensor data to a predetermined baseline and comparing a difference between the sensor data and the predetermined baseline to at least one predetermined symptom threshold;
weigh each of the symptom metrics to form a composite metric indicative of the likelihood that the user is likely to have contracted the disease; and
determine whether the user is likely to have contracted the disease by comparing the composite metrics to one or more predetermined composite thresholds, wherein:
the plurality of symptoms include anosmia or ageusia; and
the sensor data comprises sound, recorded by a microphone, that is analyzed using speech detection algorithms to identify phrases in the recorded sound indicative of anosmia or ageusia.

6. The system of claim 5, further comprising:
a graphical user interface that provides functionality to identify the plurality of symptoms of the disease, adjust one or more of the predetermined symptom thresholds, adjust the weights of one or more of the symptom metrics, and/or adjust the one or more predetermined composite thresholds for each symptom of the disease identified via the graphical user interface.

7. The system of claim 5, wherein, in response to a determination that the user is likely to have contracted the disease, the instructions further cause the system to:
identify additional devices in the location of the user device; and
output information to the users of the additional devices.

8. The system of claim 7, wherein receiving the locations of the user device and identifying additional devices in the location of the user device comprises:
identifying the additional devices within range of the user device via direct, short range, wireless communication signals; or
identifying local area networks joined by the user device and the additional devices joined to the local area network.

* * * * *